US011312985B2

(12) United States Patent
Tao et al.

(10) Patent No.: US 11,312,985 B2
(45) Date of Patent: Apr. 26, 2022

(54) ENZYMATIC METHOD FOR PREPARING REBAUDIOSIDE C

(71) Applicant: PepsiCo, Inc., Purchase, NY (US)

(72) Inventors: Alex Tao, Jiangsu (CN); Guoqing Li, Jiangsu (CN); Wenxia Wang, Jiangsu (CN); Leilei Zheng, Jiangsu (CN); Chunlei Zhu, Jiangsu (CN); Xiaoliang Liang, Jiangsu (CN); Kuikiu Chan, Jiangsu (CN)

(73) Assignee: PepsiCo, Inc., Purchase, NY (US)

( * ) Notice: Subject to any disclaimer, the term of this patent is extended or adjusted under 35 U.S.C. 154(b) by 256 days.

(21) Appl. No.: 16/343,339

(22) PCT Filed: Oct. 21, 2016

(86) PCT No.: PCT/CN2016/102910
§ 371 (c)(1),
(2) Date: Apr. 18, 2019

(87) PCT Pub. No.: WO2018/072203
PCT Pub. Date: Apr. 26, 2018

(65) Prior Publication Data
US 2019/0367960 A1 Dec. 5, 2019

(51) Int. Cl.
C12P 19/18 (2006.01)
C12P 19/56 (2006.01)
C12N 9/10 (2006.01)

(52) U.S. Cl.
CPC ............ C12P 19/56 (2013.01); C12N 9/10 (2013.01); C12Y 204/01 (2013.01)

(58) Field of Classification Search
CPC ........... C12P 19/56; C12P 19/44; C12P 15/00; C12N 9/1051; A23V 2250/258; C12Y 204/01013; C12Y 204/01
USPC .................... 435/78, 94, 200, 193, 252.3
See application file for complete search history.

(56) References Cited

U.S. PATENT DOCUMENTS

| 9,243,273 | B2 | 1/2016 | Markosyan et al. |
| 9,752,174 | B2 | 9/2017 | Markosyan |
| 10,301,662 | B2 | 5/2019 | Tao et al. |
| 2010/0099857 | A1 | 4/2010 | Evans |
| 2011/0218161 | A1 | 9/2011 | Han et al. |
| 2013/0171328 | A1 | 7/2013 | Kishore et al. |
| 2014/0357588 | A1 | 12/2014 | Markosyan |
| 2016/0186225 | A1 | 6/2016 | Mikkelsen |
| 2016/0298159 | A1 | 10/2016 | Tao et al. |
| 2017/0211113 | A1 | 7/2017 | Tao et al. |
| 2018/0320211 | A1 | 11/2018 | Du et al. |

FOREIGN PATENT DOCUMENTS

| AU | 2015/261617 A1 | 12/2015 |
| CA | 2 913 252 A1 | 12/2014 |
| CN | 103031283 A | 4/2013 |
| CN | 103088041 A | 5/2013 |
| CN | 103179850 A | 6/2013 |
| CN | 103397064 A | 11/2013 |
| CN | 106471128 A | 1/2014 |
| CN | 103732753 A | 4/2014 |
| CN | 103757074 A | 4/2014 |
| CN | 105200098 A | 12/2015 |
| CN | 105492453 A | 4/2016 |
| JP | 2010-538621 | 12/2010 |
| JP | 2012-504552 A | 2/2012 |
| JP | 2014524247 A | 9/2014 |
| JP | 2016527892 A | 9/2016 |
| RU | 2 596 190 C9 | 10/2016 |
| WO | WO 2010/038911 A1 | 4/2010 |
| WO | WO 2011/046423 A1 | 4/2011 |
| WO | WO 2011/153378 A1 | 12/2011 |
| WO | WO 2012/103074 A2 | 8/2012 |
| WO | WO 2013/022989 A2 | 2/2013 |
| WO | WO 2013/096420 A1 | 6/2013 |
| WO | WO 2013/110673 A1 | 8/2013 |
| WO | WO 2013/176738 A1 | 11/2013 |
| WO | WO 2014/086890 A1 | 6/2014 |
| WO | WO 2014/122227 A2 | 8/2014 |
| WO | WO-2014193934 A1 | 12/2014 |
| WO | WO 2015/021690 A1 | 2/2015 |
| WO | WO 2015/094117 A1 | 6/2015 |
| WO | WO 2015/113231 A1 | 8/2015 |
| WO | WO2016/028899 A1 | 2/2016 |
| WO | WO 2016/196345 A1 | 12/2016 |
| WO | WO 2017/031424 A1 | 2/2017 |

OTHER PUBLICATIONS

Genbank, "UDP-glycosyltransferase 76G1 [Stevia rebaudiana]," Accession No. AAR06912.1, accessed at http://www.ncbi.nlm.nih.gov/protein/AAR06912, accessed on May 26, 2016, 2 pages.
Genbank, "Os03g0702000 [Oryza saliva Japonica Group]," Accession No. NP_001051007.2, accessed at http://www.ncbi.nlm.nih.gov/protein/NP_001051007.2?report=genpept, accessed on May 26, 2016, 4 pages.
Masada, S., et al., "An efficient chemoenzymatic production of small molecule glucosides with in situ UDP-glucose recycling," FEBS Letters 581(13):2562-2566, Elsevier B.V., Netherlands (2007).
Ohta, M., et al., "Characterization of Novel Steviol Glycosides from Leaves of Stevia rebaudiana Morita," J. Appl. Glycosci. 57(3):199-209, The Japanese Society of Applied Glycoscience, Japan (2010).
Wang, Q.J., et al., "Saccharomyces cerevisiae surface expression of sucrose synthase," China resources biotechnology and enzyme engineering symposium proceedings (2005).

(Continued)

Primary Examiner — Robert B Mondesi
Assistant Examiner — Mohammad Y Meah
(74) Attorney, Agent, or Firm — Sterne, Kessler, Goldstein & Fox P.L.L.C.

(57) ABSTRACT

Provided is a method for preparing Rebaudioside C using an enzymatic method, comprising using rubusoside or dulcoside A as a substrate, and making the substrate, in the presence of a glycosyl donor, react under the catalysis of UDP-glycosyltransferase-containing recombinant cell and/or UDP-glycosyltransferase prepared therefrom to generate Rebaudioside C.

8 Claims, No Drawings

Specification includes a Sequence Listing.

(56) References Cited

OTHER PUBLICATIONS

Wölwer-Rieck, U., "The leaves of *Stevia rebaudiana* (Bertoni), their constituents and the analyses thereof: a review," *J Agric Food Chem.* 60(4):886-895, American Chemical Society, United States (2012).

Co-pending, U.S. Appl. No. 16/343,335, inventors Tao, A., et al., filed Oct. 21, 2016 (Not Published).

Pearson, W.R., "An Introduction to Sequence Similarity ("Homology") Searching," *Curr Protoc Bioinformatic*, Author Manuscript, Jun. 3, Wiley, USA (2013).

Whisstock et al., "Prediction of protein function from protein sequence and stucture," Quarterly Reviews of Biophysics, 36(3): 307-340 (2003).

Witkowski et al., "Conversion of a beta-ketoacyl synthase to a malonyl decarboxylase by replacement of the active-site cysteine with glutamine," Biochemistry 38(36): 11643-11650 (1999).

Chen, R.R., "Permeability issues in whole-cell bioprocesses and cellular membrane engineering," Appl Microbial Biotechnol 74:730-738 (2007).

UniProtKB—F2DT21 (F2DT21_HORVD), May 31, 2011, accessed at http://www.uniprot.org/uniprot/F2DT21, 4 pages.

Co-pending, U.S. Appl. No. 15/932,218, inventors Anderson, A., et al., filed Aug. 19, 2016 (Not Published).

Co-pending, U.S. Appl. No. 16/380,678, inventors Tao, J., et al., filed Apr. 10, 2019 (Not Published).

Son, M.H. et al., "Production of Flavonoid O-Glucoside Using Sucrose Synthase and Flavonoid O-Glucosyltransferase Fusion Protein," J. Microbiol. Biotechnol. 19(7):709-12, Springer Nature, Switzerland (2009).

Mohamed, A.A. et al., "UDP-dependent glycosyltransferases involved in the biosynthesis of steviol glycosides," J Plant Physiol. 168(10):1136-41, Elsevier, Netherlands (2011).

Branden, C. et al., "Prediction, Engineering, and Design of Protein Structures," Introduction to Protein Structure, Garland Publishing Inc., New York, p. 247 (1991).

Studer, R.A. et al., "Residue mutations and their impact on protein structure and function:detecting beneficial and pathogenic changes," Biochem. J. 449:581-594, Biochemical Society, England (2013).

Co-pending, U.S. Appl. No. 16/343,340, inventors Tao, A., et al., filed Oct. 21, 2016 (Not Published).

Xu, L. et al., "Progress and strategies on bioethanol production from liganocellulose by consolidated bioprocessing (CBP) using *Saccharyomyces cerevisiae*," *Chinese Journal of Biotechnology* 26(7): 870-9 (2010).

English Translation of the Written Opinion for International Application No. PCT/CN2016/102948, State Intellectual Property Office of the P.R. China, China, dated Jul. 18, 2017, 3 pages.

English Translation of the International Preliminary Report on Patentability for International Application No. PCT/CN2016/102948, State Intellectual Property Office of the P.R. China, China, dated Apr. 23, 2019, 4 pages.

English Translation of the Written Opinion for International Application No. PCT/CN2016/102910, State Intellectual Property Office of the P.R. China, China, dated Jul. 14, 2017, 3 pages.

English Translation of the International Preliminary Report on Patentability for International Application No. PCT/CN2016/102910, State Intellectual Property Office of the P.R. China, China, dated Apr. 23, 2019, 4 pages.

English Translation of the Written Opinion for International Application No. PCT/CN2016/102942, State Intellectual Property Office of the P.R. China, China, dated Jul. 12, 2017, 4 pages.

English Translation of the International Preliminary Report on Patentability for International Application No. PCT/CN2016/102942, State Intellectual Property Office of the P.R. China, China, dated Apr. 23, 2019, 5 pages.

Ariga, O. et al., "Mechanical and kinetic properties of PVA hydrogel immobilizing beta-galactosidase," *Journal of Fermentation and Bioengineering* 76(3):203-206, Society of Fermentation Technology, Japan (1993).

Supplementary European Search Report for EP Application No. EP 16 91 9508, Berlin, Germany, dated May 27, 2020, 3 pages.

SEQUENCE LISTING

```
<160> NUMBER OF SEQ ID NOS: 4

<210> SEQ ID NO 1
<211> LENGTH: 1377
<212> TYPE: DNA
<213> ORGANISM: Artificial Sequence
<220> FEATURE:
```

<223> OTHER INFORMATION: Stevia

<400> SEQUENCE: 1

| | | | | | |
|---|---|---|---|---|---|
| atggaaaaca | aaaccgaaac | cacggtacgc | cgtcgtcgtc | gtatcatcct | cttcccggtt | 60 |
| ccgtttcagg | gtcacatcaa | cccgatcctt | cagttggcaa | acgtactgta | ctctaaaggt | 120 |
| tttagcatca | ccattttca | cactaacttt | aacaaaccga | aacctctaa | ctatccgcac | 180 |
| ttcactttcc | gcttcatcct | ggacaacgac | ccgcaagatg | agcgcattag | caacctgccg | 240 |
| acccatggcc | cgctggcagg | catgcgcatc | cctatcatca | atgaacacgg | cgctgacgaa | 300 |
| ctgcgtcgtg | agctggaact | cctgatgctg | gcttctgaag | aagacgagga | agtgtcttgc | 360 |
| ctgattacag | acgctctctg | gtactttgct | cagagcgtgg | cggactctct | gaacctgcgc | 420 |
| cgtctggttc | ttatgacttc | ttccttgttt | aatttccatg | cgcatgtctc | tctgccgcag | 480 |
| ttcgacgagc | tgggctacct | ggacccggat | gacaaaactc | gcctggagga | acaggcatct | 540 |
| ggcttcccga | tgctgaaagt | aaaagatatc | aaaagcgcat | actccaattg | gcagatcctg | 600 |
| aaagagattc | tgggcaaaat | gatcaagcag | actaaagcat | ccagcggcgt | tatctggaac | 660 |
| tcctttaaag | agctggagga | aagcgaactg | gaaaccgtga | tccgtgaaat | cccggcaccg | 720 |
| tcgttcctga | ttcctctgcc | taaacatctg | accgcctcct | cttcttctct | gctggatcac | 780 |
| gatcgcaccg | ttttccagtg | gctggatcag | caaccgccga | ttctgtgct | gtatgtttct | 840 |
| ttcggctcga | cgagtgaggt | tgacgaaaaa | gacttcctgg | aaatcgcacg | cggcctggtt | 900 |
| gactctaaac | agagctttct | gtgggttgta | cgtccgggtt | tcgtgaaggg | cagcacctgg | 960 |
| gttgaaccgc | tgccgacgg | cttttttggc | gaacgcggcc | gtatcgtaaa | atgggtaccg | 1020 |
| cagcaggagg | tactggcaca | cggcgcaatt | ggggcgttct | ggactcactc | cggctggaac | 1080 |
| tccactctgg | aatccgtatg | cgaaggcgtt | cctatgattt | tcagcgactt | cggcctggat | 1140 |
| cagccgctga | acgcacgcta | tatgtcagac | gttctgaaag | tcggtgtgta | tctggagaac | 1200 |
| gggtgggagc | gtggcgaaat | tgccaacgcg | atccgtcgtg | ttatggtgga | tgaagaaggc | 1260 |
| gaatacatcc | gtcagaacgc | tcgtgtcctt | aaacagaaag | ctgacgtgag | cctgatgaaa | 1320 |
| ggtggctcta | gctacgaatc | gctggagtcc | ctggtttctt | acatctcgtc | gctgtaa | 1377 |

<210> SEQ ID NO 2
<211> LENGTH: 458
<212> TYPE: PRT
<213> ORGANISM: Artificial Sequence
<220> FEATURE:
<223> OTHER INFORMATION: Stevia

<400> SEQUENCE: 2

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser

|     |     |     |     | 100 |     |     |     |     | 105 |     |     |     |     | 110 |     |
| --- | --- | --- | --- | --- | --- | --- | --- | --- | --- | --- | --- | --- | --- | --- | --- |
Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
        130                 135             140

Met Thr Ser Ser Leu Phe Asn Phe His Ala His Val Ser Leu Pro Gln
145             150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225             230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
        290                 295                 300

Ser Phe Leu Trp Val Val Arg Pro Gly Phe Val Lys Gly Ser Thr Trp
305             310                 315                 320

Val Glu Pro Leu Pro Asp Gly Phe Leu Gly Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385             390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
        450                 455

<210> SEQ ID NO 3
<211> LENGTH: 1389
<212> TYPE: DNA
<213> ORGANISM: Artificial Sequence
<220> FEATURE:
<223> OTHER INFORMATION: rice

<400> SEQUENCE: 3
atggacagcg gttactcttc tagctatgct gcggcagccg gtatgcacgt agttatttgt        60

-continued

```
ccgtggctcg ctttcggtca cctcctgccg tgcctggacc tggcgcagcg cctggcatct    120
cgtggtcacc gtgtcagttt cgttagcacg ccgcgtaaca tctcacgtct gccgccggtc    180
cgtccggctc tggccccgct ggttgcgttc gttgcgctac ctctgccgcg cgttgaaggc    240
ttaccggatg gcgcagagtc taccaacgac gtgccgcacg atcgcccgga tatggttgaa    300
ctccaccgcc gtgcatttga cggtctggca gctccgttct ccgaatttct gggtaccgcg    360
tgtgccgact gggtcatcgt agacgtattc caccactggg cagctgcagc ggctttagaa    420
cacaaagtac cgtgcgcaat gatgctgctg ggctctgctc acatgatcgc gtctattgcc    480
gaccgtcgtc tggaacgtgc agagaccgaa tctccagcgg cagccggtca gggccgtcct    540
gcagctgctc cgaccttcga agttgctcgt atgaagctca tccgcactaa aggttcttcc    600
ggtatgtcac tggcagagcg tttctcgctg acgctctccc gtagcagcct ggttgtgggg    660
cgctcctgcg tggaattcga accggaaact gtgccgctac tgtctaccct gcgtggcaag    720
ccgatcactt ttctgggtct catgccgcca ctgcacgaag gtcgccgcga agacggtgaa    780
gatgctacgg ttcgttggtt ggacgcccag ccggctaaaa gcgtcgtgta cgtagctctg    840
ggcagtgaag ttccattggg tgtcgagaaa gtgcatgaac tggctttggg tctggagctg    900
gctggcaccc gtttcctctg ggcactgcgt aagccgactg gtgtgtctga tgctgacctt    960
ctgccggctg gtttcgaaga acgtacccgt ggtcgcggcg tagtggcaac ccgctgggta   1020
ccgcagatgt ccatcctggc acacgctgct gttggcgcgt tcttaccca ctgcgggtgg    1080 aactctacaa tcgaaggcct gatgttcggc catcctctga ttatgctgcc aatcttcggt   1140
gatcagggtc cgaacgctcg tctgatcgaa gccaaaaacg ccggcttaca agtcgcacgc   1200
aacgacggcg atggttcttt cgatcgtgaa ggtgttgcgg cagctatccg tgcagtggct   1260
gtagaagaag agtcgagcaa agtgttccag gcaaaagcca aaaagctgca ggaaatcgtt   1320
gcggacatgg cgtgccacga acgttacatc gatggcttta ccagcagct gcgctcctac    1380 aaagattaa                                                            1389
```

<210> SEQ ID NO 4
<211> LENGTH: 462
<212> TYPE: PRT
<213> ORGANISM: Artificial Sequence
<220> FEATURE:
<223> OTHER INFORMATION: rice

<400> SEQUENCE: 4

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
```

```
                115             120             125
Val Phe His His Trp Ala Ala Ala Ala Leu Glu His Lys Val Pro
    130             135             140

Cys Ala Met Met Leu Leu Gly Ser Ala His Met Ile Ala Ser Ile Ala
145             150             155             160

Asp Arg Arg Leu Glu Arg Ala Glu Thr Glu Ser Pro Ala Ala Ala Gly
                165             170             175

Gln Gly Arg Pro Ala Ala Ala Pro Thr Phe Glu Val Ala Arg Met Lys
            180             185             190

Leu Ile Arg Thr Lys Gly Ser Ser Gly Met Ser Leu Ala Glu Arg Phe
        195             200             205

Ser Leu Thr Leu Ser Arg Ser Ser Leu Val Val Gly Arg Ser Cys Val
    210             215             220

Glu Phe Glu Pro Glu Thr Val Pro Leu Leu Ser Thr Leu Arg Gly Lys
225             230             235             240

Pro Ile Thr Phe Leu Gly Leu Met Pro Pro Leu His Glu Gly Arg Arg
                245             250             255

Glu Asp Gly Glu Asp Ala Thr Val Arg Trp Leu Asp Ala Gln Pro Ala
            260             265             270

Lys Ser Val Val Tyr Val Ala Leu Gly Ser Glu Val Pro Leu Gly Val
        275             280             285

Glu Lys Val His Glu Leu Ala Leu Gly Leu Glu Leu Ala Gly Thr Arg
    290             295             300

Phe Leu Trp Ala Leu Arg Lys Pro Thr Gly Val Ser Asp Ala Asp Leu
305             310             315             320

Leu Pro Ala Gly Phe Glu Arg Thr Arg Gly Arg Gly Val Val Ala
                325             330             335

Thr Arg Trp Val Pro Gln Met Ser Ile Leu Ala His Ala Ala Val Gly
            340             345             350

Ala Phe Leu Thr His Cys Gly Trp Asn Ser Thr Ile Glu Gly Leu Met
        355             360             365

Phe Gly His Pro Leu Ile Met Leu Pro Ile Phe Gly Asp Gln Gly Pro
    370             375             380

Asn Ala Arg Leu Ile Glu Ala Lys Asn Ala Gly Leu Gln Val Ala Arg
385             390             395             400

Asn Asp Gly Asp Gly Ser Phe Asp Arg Glu Gly Val Ala Ala Ala Ile
                405             410             415

Arg Ala Val Ala Val Glu Glu Glu Ser Ser Lys Val Phe Gln Ala Lys
            420             425             430

Ala Lys Lys Leu Gln Glu Ile Val Ala Asp Met Ala Cys His Glu Arg
        435             440             445

Tyr Ile Asp Gly Phe Ile Gln Leu Arg Ser Tyr Lys Asp
    450             455             460
```

ENZYMATIC METHOD FOR PREPARING REBAUDIOSIDE C

REFERENCE TO SEQUENCE LISTING SUBMITTED ELECTRONICALLY

The content of the electronically submitted sequence listing, (file name: 3711_9310000_SequenceListing.txt; size: 12,237 bytes; and date of creation: Apr. 15, 2019), filed herewith, is incorporated herein by reference in its entirety.

FIELD OF INVENTION

The present invention relates to a method for preparing Rebaudioside C, in particular to a biological preparation method of Rebaudioside C.

BACKGROUND

Sweetening agents are a class of food additives that have wide applications in the production of food, beverages, and candies. They may be added in the food production process, or alternatively may be used through appropriate dilution as a substitute for sucrose in household baking. Sweetening agents include natural sweetening agents, for example, sucrose, high fructose corn syrup, honey, etc., and artificial sweetening agents, for example, aspartame, saccharine, etc. Steviosides are a class of natural sweetening agents extracted from the plant *Stevia rebaudiana*, and are widely used in food products and beverages at present. The extract of *Stevia rebaudiana* contains a variety of steviosides comprising Rebaudioside. Naturally extracted steviosides vary widely in composition across different batches, and need subsequent purification.

In the conventional method of producing Rebaudioside C, Rebaudioside C is extracted from *Stevia rebaudiana* leaves. For example, as disclosed in U.S. Pat. No. 8,501,261, about 111 g of product with 87.6% purity can be obtained by extracting from 10 kg of *Stevia rebaudiana* leaves. Because the percentage of Rebaudioside C found in *Stevia rebaudiana* leaves is relatively lower (about 10% of the total dry weight), the production cost of Rebaudioside C is relatively higher than that of Rebaudioside A (about 60% of the total dry weight). Furthermore, because of the limited yield, the commercial application of Rebaudioside C is hindered.

SUMMARY

The technical problem to be solved by the present invention is to overcome the defects of the prior art. The present invention achieves so by providing a method for preparing Rebaudioside C using an enzymatic method. With such a method, Rebaudioside C product with high purity can be produced at a lower cost and a shorter productuin cycle.

The following technical solution is employed by the present invention to solve the technical problem described above.

A method for preparing Rebaudioside C using an enzymatic method. In the method, dulcoside A is used as a substrate; and in the presence of a glycosyl donor, Rebaudioside C is produced by means of a reaction under the catalysis of recombinant cells containing UDP-glycosyltransferase and/or UDP-glycosyltransferase prepared therefrom.

A method for preparing Rebaudioside C using an enzymatic method. In the method, rubusoside is used as a substrate; and in the presence of a glycosyl donor, Rebaudioside C is produced by means of a reaction under the catalysis of recombinant cells containing UDP-glycosyltransferase and/or UDP-glycosyltransferase prepared therefrom.

Preferably, the glycosyl donor comprises one or two of glucosyl donor and rhamnosyl donor, the glucosyl donor is UDP-glucose or a UDP-glucose regeneration system (2007, *FEBS Letters*, 581, 2562-2566) consisting of sucrose, sucrose synthase and UDP, and the rhamnosyl donor is UDP-rhamnose. Herein, a UDP-glucose regeneration system consisting of sucrose, sucrose synthase and UDP is preferred. The price of UDP-glucose is higher. The cost can be greatly reduced by using the UDP-glucose regeneration system.

Preferably, the UDP-glucosyltransferase (i.e., uridine diphosphate glucosyltransferase, UGT for short, which has been known) comprises one or two of UGT-A from *Stevia rebaudiana* and UGT-B from *Oryza sativa*.

Preferably, the UDP-glucosyltransferase is UGT-A from *Stevia rebaudiana*, and the amino acid sequence of the UGT-A is at least 60% consistent with Sequence 2 as shown in the Sequence Listing.

More preferably, the amino acid sequence of the UGT-A is at least 70% consistent with Sequence 2 as shown in the Sequence Listing.

Further, the amino acid sequence of the UGT-A is at least 80% consistent with Sequence 2 as shown in the Sequence Listing.

Further, the amino acid sequence of the UGT-A is at least 90% consistent with Sequence 2 as shown in the Sequence Listing.

According to one specific aspect, the amino acid sequence of the UGT-A is fully consistent with Sequence 2 in the Sequence Listing.

Preferably, the UDP-glucosyltransferase comprises UGT-A from *Stevia rebaudiana* and UGT-B from *Oryza sativa*; the UDP-glycosyltransferase is added into the reaction system in two steps, the UGT-B is firstly added in the first step and the UGT-A is then added in the second step.

Preferably, the amino acid sequence of the UGT-A is at least 60% consistent with Sequence 2 as shown in the Sequence Listing; and/or the amino acid sequence of the UGT-B is at least 60% consistent with Sequence 4 as shown in the Sequence Listing.

More preferably, the amino acid sequence of the UGT-A is at least 70% consistent with Sequence 2 as shown in the Sequence Listing; and/or the amino acid sequence of the UGT-B is at least 70% consistent with Sequence 4 as shown in the Sequence Listing.

Further, the amino acid sequence of the UGT-A is at least 80% consistent with Sequence 2 as shown in the Sequence Listing; and/or the amino acid sequence of the UGT-B is at least 80% consistent with Sequence 4 as shown in the Sequence Listing.

Further, the amino acid sequence of the UGT-A is at least 90% consistent with Sequence 2 as shown in the Sequence Listing; and/or the amino acid sequence of the UGT-B is at least 90% consistent with Sequence 4 as shown in the Sequence Listing.

According to the present invention, the reaction may be carried out in an aqueous system with temperature of 4-50° C. and pH of 5.0-9.0. Preferably, the reaction is carried out in an aqueous system with temperature of 34-45° C. and pH of 7.5-8.5.

More preferably, the reaction is carried out in a phosphoric acid buffer solution.

More preferably, the reaction system comprises the recombinant cells containing UDP-glycosyltransferase and a cell-permeable agent. Further, the cell-permeable agent is toluene, and the volume specific concentration of toluene in the reaction system is 1-3%.

More preferably, all raw materials used for reaction are added to a reaction kettle to be uniformly mixed and then placed at a set temperature for reaction while stirring. After reaction is completed, the product Rebaudioside C can be obtained through purification. A specific purification method is a post-treatment including resin separation. According to this purification method, the product Rebaudioside C with purity up to 95% can be obtained.

Preferably, the recombinant cells are microorganism cells. More preferably, the microorganism is *Escherichia coli*, *Saccharomyces cerevisiae* or *Pichia pastoris*.

According to one specific aspect of the present invention, in the first-step reaction, the substrate is rubusoside, the UDP-glycosyltransferase is UGT-B from *Oryza sativa*, and the sequence of the amino acid of UGT-B from *Oryza sativa* is at least 80% consistent with Sequence 4. In the second-step reaction, the substrate is reaction solution containing the product dulcoside A in the first-step reaction, the UDP-glycosyltransferase is UGT-A from *Stevia rebaudiana*, and the sequence of the amino acid of UGT-A from *Stevia rebaudiana* is at least 80% consistent with Sequence 2.

According to another aspect of the present invention, the substrate is dulcoside A, the UDP-glycosyltransferase is UGT-A from *Stevia rebaudiana*, and the sequence of the amino acid of UGT-A from *Stevia rebaudiana* is at least 80% consistent with Sequence 2.

Compared with the prior art, the present invention has the following advantages by performing the foregoing technical solution:

The method for preparing Rebaudioside C using the enzymatic method provided by the present invention has important application values. Because the growth rate of microorganisms is much faster than that of plants, by adopting the method provided by the present invention, the production cost can be greatly reduced, the production cycle is shortened, and the competitiveness of the product is greatly improved. In addition, since the content of steviosides in plants is low and there are many steviosides with different structures, it is very difficult to extract pure products. Compared with the existing methods for extracting Rebaudioside C from *Stevia rebaudiana* leaves, by adopting the method using the enzymatic method as provided in the present invention, products with higher purity can be extracted. The products can thus be more economically applied in the food industry such as in beverages. Furthermore, the application scope of Rebaudioside C will be further expanded.

DETAILED DESCRIPTION OF THE INVENTION

For structural formulas of rubusoside, dulcoside A and Rebaudioside C, respectively refer to formulas I, II and III.

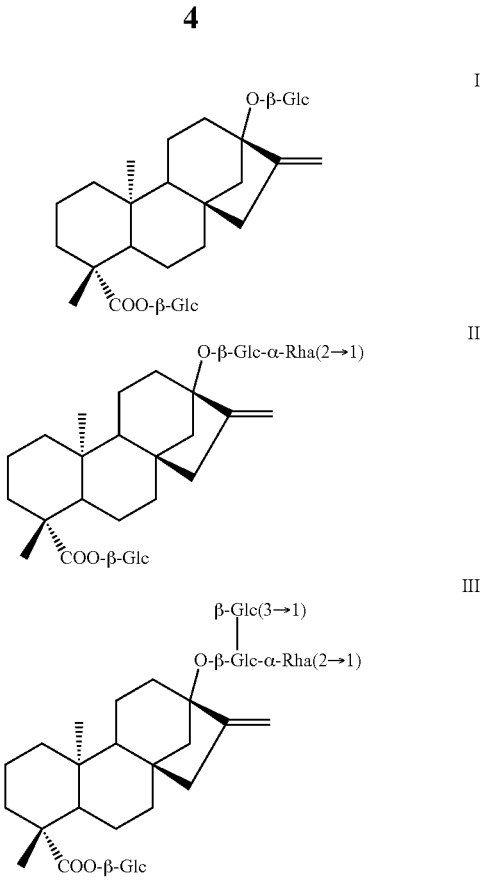

The present invention mainly provides two routes for synthesizing Rebaudioside C:

Route One:

Route Two:

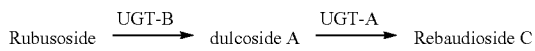

The UGT-A or UGT-B used in the present invention may exist in the form of lyophilized enzyme powder or in the recombinant cells.

The method for obtaining UGT-A or UGT-B is as follows:

A recombinant *Escherichia coli* (or its microorganism) expression strain of UGT-A or UGT-B is obtained by utilizing a molecular cloning technique and genetic engineering technique; then the recombinant *Escherichia coli* is fermented to obtain recombinant cells containing UGT-A or UGT-B, or lyophilized powder of UGT-A or UGT-B is prepared by the recombinant cells.

The molecular cloning technique and genetic engineering technique described herein are known ones, unless otherwise specified. For the molecular cloning technique, refer to *Molecular Cloning: A Laboratory Manual* (3rd Edition) (by J. Sambrook, 2005)

The expression steps of the recombinant strain herein constructed by employing a genetic engineering technique are as follows:

(1) (According to Sequences 1 and 2 as shown in the Sequence Listing, or according to Sequences 3 and 4), needed gene fragments are genetically synthesized, linked into a vector pUC57, and added with restriction enzyme digestion sites NdeI and BamHI at both ends.

(2) Each gene fragment is inserted into the corresponding restriction enzyme digestion site of an expression vector pET30a through double enzyme digestion and linking such that each gene is placed under the control of a promoter T7;

(3) Recombinant plasmids are transformed into *Escherichia coli* BL21 (DE3) and the expression of the target protein is induced by using IPTG to obtain a recombinant *Escherichia coli* expression strain of UGT-A or UGT-B.

Recombinant cells containing UGT-A or UGT-B, or lyophilized powder of UGT-A or UGT-B is prepared by utilizing the recombinant *Escherichia coli* expression strain containing UGT-A or UGT-B.

The recombinant *Escherichia coli* expression strain containing UGT-A or UGT-B is inoculated into 4 ml of liquid LB culture medium according to a ratio of 1%, shaking culture is carried out at 37° C. (200 rpm) for one night, the culture stood for one night is transferred into 50 ml of liquid LB culture medium according to an inoculation amount of 1%, shaking culture is carried out at 37° C. (200 rpm) till the OD600 value reaches 0.6-0.8, MIPTG with final concentration of 0.4 mM is added, and shaking culture is carried out at 20° C. for one night. After induction, cells are collected by means of centrifugation (8,000 rpm, 10 min), the cells are resuspended with 5 ml of 2 mmol/L phosphate buffer solution (pH7.0) to obtain the recombinant cells, the cells are further ultrasonically disrupted in an ice bath, the disruption liquid is centrifuged (8,000 rpm, 10 min), and the supernatant is collected and lyophilized for 24 h to obtain the lyophilized powder.

The present invention will be described below in more detail in connection with specific examples.

Example 1: Preparation of Recombinant *Saccharomyces cerevisiae* Cells Containing UGT-A According to Sequences 1 and 2 as shown in the Sequence Listing, gene fragments containing UGT-A were genetically synthesized, added with restriction enzyme digestion sites NdeI and BamHI at both ends, and linked into a vector pUC57 (produced by SUZHOU GENEWIZ BIOTECHNOLOGY CO., LTD.). The UGT gene fragments were digested by restriction enzyme NdeI and BamHI, purified fragments were recovered, and T4 ligase was added to link the fragments to the corresponding restriction enzyme digestion sites pET30a, so as to transform it into a BL21 (DE3) strain.

The UGT strain was inoculated into 4 ml of liquid LB culture medium according to a ratio of 1%, shaking culture was carried out at 37° C. (200 rpm) for one night, the culture stood for one night was transferred into 50 ml of liquid LB culture medium according to an inoculation amount of 1%, shaking culture was carried out at 37° C. (200 rpm) till the $OD_{600}$ value reached 0.6-0.8, MIPTG with final concentration of 0.4 mM was added, and shaking culture was carried out at 20° C. for one night. After induction, cells were collected by means of centrifugation (8,000 rpm, 10 min), and the cells were resuspended with 5 ml of 2 mmol/L phosphate buffer solution (pH7.0) to obtain the recombinant cells containing UGT-A for catalysis.

Example 2: Preparation of Lyophilized Powder of UGT-A

The recombinant cells containing UGT-A prepared in example 1 were ultrasonically disrupted in an ice bath, the disruption liquid was centrifuged (8,000 rpm, 10 min), and the supernatant was collected and lyophilized for 24 h to obtain lyophilized powder of UGT-A.

Example 3: Preparation of Recombinant *Saccharomyces cerevisiae* Cells Containing UGT-B According to Sequences 3 and 4, gene fragments containing UGT-B were genetically synthesized, added with restriction enzyme digestion sites NdeI and BamHI at both ends, and linked into a vector pUC57 (produced by SUZHOU GENEWIZ BIOTECHNOLOGY CO., LTD.). The UGT gene fragments were digested by restriction enzyme NdeI and BamHI, purified fragments were recovered, and T4 ligase was added to link the fragments to the corresponding restriction enzyme digestion sites pET30a, so as to transform it into a BL21 (DE3) strain.

The UGT strain was inoculated into 4 ml of liquid LB culture medium according to a ratio of 1%, shaking culture was carried out at 37° C. (200 rpm) for one night, the culture stood for one night was transferred into 50 ml of liquid LB culture medium according to an inoculation amount of 1%, shaking culture was carried out at 37° C. (200 rpm) till the $OD_{600}$ value reached 0.6-0.8, MIPTG with final concentration of 0.4 mM was added, and shaking culture was carried out at 20° C. for one night. After induction, cells were collected by means of centrifugation (8,000 rpm, 10 min), and the cells were resuspended with 5 ml of 2 mmol/L phosphate buffer solution (pH7.0) to obtain the recombinant cells containing UGT-B for catalysis.

Example 4: Preparation of Lyophilized Powder of UGT-B

The recombinant cells containing UGT-B prepared in example 3 were ultrasonically disrupted in an ice bath, the disruption liquid was centrifuged (8,000 rpm, 10 min), and the supernatant was collected and lyophilized for 24 h to obtain lyophilized powder of UGT-B.

Example 5: Synthesis of Rebaudioside C Under Catalysis of UDP-Glycosyltransferase by Using Dulcoside A as the Substrate (Route 1)

In this example, UGT-A lyophilized powder prepared according to the method in example 2 was used to catalyze the synthesis of Rebaudioside C. In this example, a UDP-glucose regeneration system consisting of sucrose, sucrose synthase from *Arabidopsis thaliana* (hereinafter referred to as AtSUS1) and UDP was used as a glucosyl donor.

In the reaction system, 1 L of 0.05 mol/L phosphate buffer solution (pH 8.0), 2 g of UDP and 8 g of dulcoside A, 50 g of sucrose, 10 g of UGT-A lyophilized powder and 3 g of AtSUS1 lyophilized powder were sequentially added and uniformly mixed, then the mixture was placed in a 40° C. water bath for 16 h, and stirring was carried out at 300 rpm for reaction. After the reaction, 500 μl of reaction solution was taken and uniformly mixed with anhydrous methanol with equal volume, centrifugation at 8,000 rpm was carried out for 10 min, the supernatant was enabled to pass through a filter membrane, and then detection was carried out by using high-performance liquid chromatography (chromatographic conditions: chromatographic column: Aglient eclipse SB-C18 4.6*150 mm; detection wavelength: 210 nm; mobile phase: 0.1% formic acid aqueous solution: acetonitrile=65%:35%; flow rate: 1.0 mL/min; column temperature: 30° C.). The conversion rate of dulcoside A was more than 90%. After the supernatant was purified by post-processing such as separation by silica gel resin and crystallization, 5.6 g of Rebaudioside C was obtained, and the purity was greater than 90%.

Example 6: Synthesis of Rebaudioside C Under Catalysis of Recombinant Cells Containing UDP-Glycosyltransferase by Using Rubusoside as the Substrate (Route 2)

In this example, UGT-A lyophilized powder prepared according to the method in example 2 and UGT-B lyophilized powder prepared according to the method in example 4 were used to catalyze the synthesis of Rebaudioside C.

First-step reaction: 1 L of 0.05 mol/L phosphate buffer solution (pH 8.0), 4.5 g of UDP rhamnose, 6.5 g of rubusoside and 10 g of UGT-B lyophilized powder were sequentially added into the reaction system, uniformly mixed and then placed in a 40° C. water bath, and stirring was carried out at 300 rpm for reaction for 16 h. Second-step reaction: after the first-step reaction, the reaction solution was boiled for 10 min, the pH value was regulated to 8.0, 2 g of UDP, 50 g of sucrose, 10 g of UGT-A lyophilized powder and 3 g of AtSUS1 lyophilized powder were added, uniformly mixed and then placed in a 40° C. water bath, and stirring was carried out at 300 rpm for reaction for 16 h. After the reaction, 500 µl of reaction solution was taken and uniformly mixed with anhydrous methanol with equal volume, centrifugation at 8,000 rpm was carried out for 10 min, the supernatant was enabled to pass through a filter membrane, and then detection was carried out by using high-performance liquid chromatography (chromatographic conditions: chromatographic column: Aglient eclipse C18 4.6*150 mm; detection wavelength: 210 nm; mobile phase: 0.1% formic acid aqueous solution: acetonitrile=65%:35%; flow rate: 1.0 mL/min; column temperature: 30° C.). The conversion rate of rubusoside was more than 90%. After the supernatant was purified by post-processing such as separation by silica gel resin and crystallization, 5.2 g of Rebaudioside C was obtained, and the purity was greater than 90%.

Example 7: Synthesis of Rebaudioside C Under Catalysis of UDP-Glycosyltransferase by Using Dulcoside A as the Substrate In this example, recombinant cells containing UGT-A prepared according to the method in example 1 were used to catalyze the synthesis of Rebaudioside C.

1 L of 0.05 mol/L phosphate buffer solution (pH 8.0), 2 g of UDP, 50 g of dulcoside A, 50 g of sucrose, 200 ml of toluene, 40 g of UGT-A whole cells and 12 g of AtSUS1 whole cells were sequentially added into the reaction system, uniformly mixed and then placed in a 40° C. water bath, and stirring was carried out at 300 rpm for reaction for 16 h. After the reaction, 500 µl of reaction solution was taken and centrifuged, the supernatant was added and uniformly mixed with anhydrous methanol with equal volume, centrifugation at 8,000 rpm was carried out for 10 min, the supernatant was enabled to pass through a filter membrane, and then detection was carried out by using high-performance liquid chromatography (chromatographic conditions: chromatographic column: Aglient eclipse SB-C18 4.6*150 mm; detection wavelength: 210 nm; mobile phase: 0.1% formic acid aqueous solution: acetonitrile=65%:35%; flow rate: 1.0 mL/min; column temperature: 30° C.). The conversion rate of dulcoside A was more than 90%. After the supernatant was purified by post-processing such as separation by silica gel resin and crystallization, 5.5 g of Rebaudioside C was obtained, and the purity was greater than 90%.

Example 8: Synthesis of Rebaudioside C Under Catalysis of Recombinant Cells Containing UDP-Glycosyltransferase by Using Rubusoside as the Substrate First-step reaction: 1 L of 0.05 mol/L phosphate buffer solution (pH 8.0), 4.5 g of UDP rhamnose, 6.5 g of rubusoside, 20 ml of toluene, and 40 g of UGT-A whole cells were sequentially added into the reaction system, uniformly mixed and then placed in a 40° C. water bath, and stirring was carried out at 300 rpm for reaction for 16 h. Second-step reaction: after the first-step reaction, the reaction solution was boiled for 10 min, the pH value was regulated to 8.0, 2 g of UDP, 50 g of sucrose, 40 g of UGT-A whole cells and 12 g of AtSUS1 whole cells were added, uniformly mixed and then placed in a 40° C. water bath, and stirring was carried out at 300 rpm for reaction for 16 h. After the reaction, 500 µl of reaction solution was taken and centrifuged, the supernatant was added and uniformly mixed with anhydrous methanol with equal volume, centrifugation at 8,000 rpm was carried out for 10 min, the supernatant was enabled to pass through a filter membrane, and then detection was carried out by using high-performance liquid chromatography (chromatographic conditions: chromatographic column: Aglient eclipse SB-C18 4.6*150 mm; detection wavelength: 210 nm; mobile phase: 0.1% formic acid aqueous solution: acetonitrile=65%:35%; flow rate: 1.0 mL/min; column temperature: 30° C.). The conversion rate of rubusoside was more than 90%. After the supernatant was purified by post-processing such as separation by silica gel resin and crystallization, 5.0 g of Rebaudioside C was obtained, and the purity was greater than 90%.

The above-described examples are merely for the illustration of the technical concept and features of the present invention; the object is only to allow those skilled in the art to understand the present invention and implement it accordingly, and the scope of the present invention is not limited thereto; any equivalent variations or modifications derived from the essence of the present invention shall fall within the protection scope of the present invention.

The invention claimed is:

1. A method for preparing Rebaudioside C, the method comprising: reacting rubusoside with a glycosyl donor in a reaction system in the presence of recombinant cells comprising UDP-glycosyltransferase and/or UDP-glycosyltransferase prepared from the recombinant cells, wherein:

the reaction system comprises toluene at a concentration by volume of 1-3%;

the UDP-glycosyltransferase has the amino acid sequence of SEQ ID NO: 2; and wherein the reaction system further comprises a UDP-glycosyltransferase having the amino acid sequence of SEQ ID NO: 4.

2. The method according to claim 1, wherein the glycosyl donor comprises a glucosyl donor and a rhamnosyl donor, wherein the glucosyl donor is UDP-glucose or a UDP-glucose regeneration system comprising sucrose, sucrose synthase, and UDP, and the rhamnosyl donor is UDP-rhamnose.

3. The method according to claim 1, wherein the UDP-glucosyltransferase comprises one or both of UGT-A from *Stevia rebaudiana* and UGT-B from *Oryza sativa*.

4. The method according to claim 1, wherein the UDP-glucosyltransferase comprises UGT-A from *Stevia rebaudiana* and UGT-B from *Oryza sativa*, and wherein the UGT-B is added in a first step and the UGT-A is added in a second step.

5. The method according to claim 1, wherein the reaction is carried out in an aqueous system with a temperature of 35-45° C. and a pH of 7.5-8.5.

6. The method according to claim 5, wherein the reaction system comprises a phosphoric acid buffer solution.

7. The method according to claim 1, wherein the recombinant cells are microorganism cells.

8. The method according to claim 7, wherein the microorganism is *Escherichia coli, Saccharomyces cerevisiae* or *Pichia pastoris*.

* * * * *